United States Patent
Lanfermann et al.

(10) Patent No.: US 8,162,857 B2
(45) Date of Patent: Apr. 24, 2012

(54) LIMB MOVEMENT MONITORING SYSTEM

(75) Inventors: Gerd Lanfermann, Aachen (DE); Richard Daniel Willmann, Siegburg (DE); Juergen Te Vrugt, Aachen (DE); Edwin Gerardus Johannus Maria Bongers, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 576 days.

(21) Appl. No.: 12/444,715

(22) PCT Filed: Oct. 8, 2007

(86) PCT No.: PCT/IB2007/054080
§ 371 (c)(1),
(2), (4) Date: Apr. 8, 2009

(87) PCT Pub. No.: WO2008/044187
PCT Pub. Date: Apr. 17, 2008

(65) Prior Publication Data
US 2010/0036288 A1    Feb. 11, 2010

(30) Foreign Application Priority Data
Oct. 11, 2006    (EP) .................................... 06122126

(51) Int. Cl.
*A61B 5/103*    (2006.01)
*A61B 5/117*    (2006.01)

(52) U.S. Cl. ...................................... 600/595

(58) Field of Classification Search ................ 600/546, 600/587–595
See application file for complete search history.

(56) References Cited

U.S. PATENT DOCUMENTS
6,487,906 B1    12/2002    Hock
6,666,831 B1    12/2003    Edgerton et al.

FOREIGN PATENT DOCUMENTS
| EP | 1547521 A2 | 6/2005 |
|---|---|---|
| EP | 1709903 A1 | 10/2006 |
| GB | 2396252 A | 6/2004 |
| JP | 2001299840 A | 10/2001 |
| WO | 03095729 A1 | 11/2003 |
| WO | 2006030230 A1 | 3/2006 |
| WO | 2006082565 A1 | 8/2006 |
| WO | 2006129273 A2 | 12/2006 |

OTHER PUBLICATIONS

Ryan, C.: "Positive Results for Robot Therapy"; News Online, Feb. 18, 2002, 4 Page Article Downloaded From http://news.bbc.co.uk/1/hi/in_depth/sci_tech/2002/boston_2002/1821609.STM.

*Primary Examiner* — Max Hindenburg
*Assistant Examiner* — Jonathan M Foreman

(57) ABSTRACT

A limb movement monitoring system, comprising a motion sensor, a garment comprising spatially addressable photonic textiles and spatially resolving pressure-sensitive textiles and furthermore a muscular activity sensor, a processing unit processing the data from the sensors and issuing illumination commands to the spatially addressable photonic textiles and a database. There is furthermore a process for monitoring limb movement by the system.

10 Claims, 1 Drawing Sheet

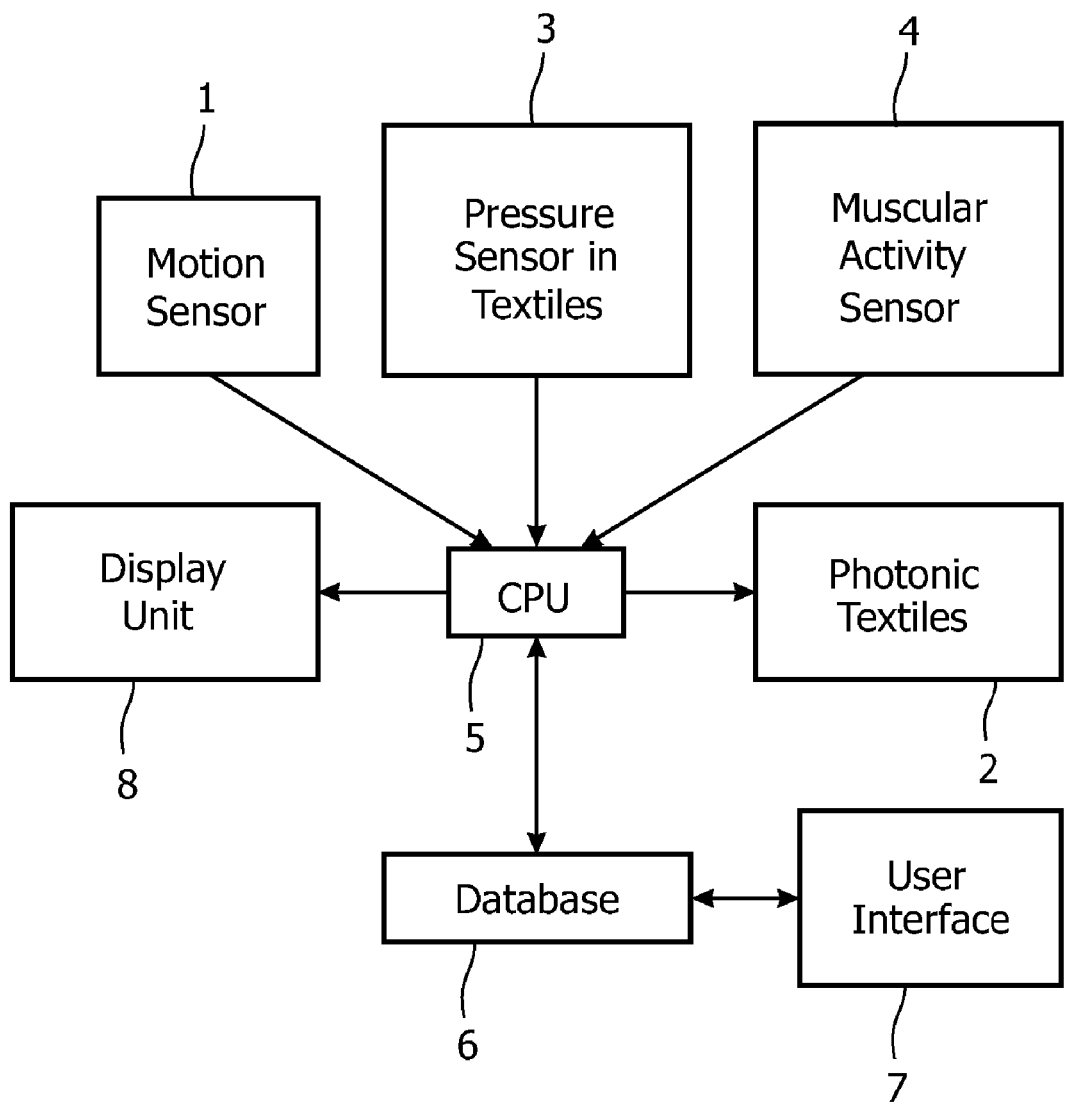

LIMB MOVEMENT MONITORING SYSTEM

BACKGROUND OF THE INVENTION

The present invention concerns a limb movement monitoring system.

Mobilizing a paretic limb, which occurs quite frequently for example after a stroke, is traditionally undertaken through hands-on physiotherapy. The therapist uses special grip techniques to move the weak arm, carefully paying attention to the limited range of motion that is often present. Such a treatment may restore the functional abilities of the affected limbs and may also reduce secondary complications like shoulder subluxations when an arm is affected. However, current budget pressure is limiting the amount of physiotherapy that can be prescribed for a person. At the same time, the administering of physiotherapy by a layperson poses its own difficulties.

U.S. Pat. No. 6,487,906 describes a sequence of low-force, high-compliance, long-extension, piezofilm-based sensors for a biofeedback system for self-monitoring of selected body motions. Flexible, large-area, piezofilm sensors are mounted on compliant but less flexible, larger-area, backbone structures so as to distribute localized stress anomalies and produce a useful, coherent, signal voltage for realtime body motion monitoring. The sensors are used in combination with body appliances that permit suitable placement of the sensors proximate to the body, in areas suitable for measuring body motion, such as twist, stretch and flexure. The sensors provide input signals to a small, self-contained signal processing and feedback module that generates a limited sequence of stepped announcements indicating the amount of motion detected. Instant feedback is provided to the user in the form of audible tones, colored lights, or other means intended to provide periphery feedback without directly interfering with the intended motion.

However, the art as taught in U.S. Pat. No. 6,487,906 is lacking in that when there is passive movement of a paretic or otherwise affected limb, the person moving the limb is not instructed in which direction the limb should be mobilized. Furthermore, an inexperienced person moving the limb is not warned when the beneficial scope of movement is exceeded, for example when mobilizing against a contracture.

SUMMARY OF THE INVENTION

A limb movement monitoring system that indicates to a person how to mobilize or exercise a paretic or otherwise affected limb of another person, while at the same time providing feedback about the limb movement, would still be desirable.

To better address one or more of these needs, a limb movement monitoring system is presented which comprises:
- a motion sensor,
- a garment comprising spatially addressable photonic textiles and spatially resolving pressure-sensitive textiles,
- a processing unit which receives data from the motion sensor and from the spatially resolving pressure-sensitive textiles and which issues illumination commands to the spatially addressable photonic textiles,
- a database in communication with the processing unit, wherein
- the database stores data from the motion sensor resolved into individual spatial descriptors and time,
- the database stores data from the pressure-sensitive textiles resolved into at least the categories of x and y coordinates and pressure,
- the database furthermore comprises comparison motion data resolved into individual spatial descriptors and time,
- the processing unit compares the motion data from the motion sensor to the comparison motion data in the database, and
- the processing unit issues illumination commands to the spatially addressable photonic textiles, based upon the deviation of the motion data from the comparison motion data and the deviation of the pressure data from a preset threshold

BRIEF DESCRIPTION OF THE DRAWINGS

FIG. 1 is a block diagram of the components of a system according to the present invention showing the interactions between them.

DETAILED DESCRIPTION OF THE INVENTION

Before the invention is described in detail, it is to be understood that this invention is not limited to the particular component parts of the devices described or process steps of the methods described, as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise.

The individual spatial descriptors in a system according to the present invention can be any parameters that are appropriate to describe the spatial position of e.g. a sensor or the orientation of a limb. For example, such individual spatial descriptors may be Cartesian coordinates (x, y, z), Euler angles or quaternions.

The motion sensor in a system according to the present invention may be an inertial sensor. The class of inertial sensors comprises, for example, accelerometers, gyroscopes and magnetometers. Accelerometers may be sensitive to the earth's gravitational field, whereas gyroscopes may be sensitive to the rate of turn.

For example, the acceleration sensor may detect acceleration along the x-, y- and z-axis. It is also possible that the acceleration sensor may detect angular acceleration, such as angular acceleration in three substantially orthogonal planes. It is also possible that the motion sensor is a combined sensor which combines, for example, a three-dimensional accelerometer, two two-dimensional gyroscopes and three one-dimensional magnetometers.

The sensor or sensors may be located at various positions on the body of the person using the limb movement monitoring system according to the present invention such as on the arms, legs and/or torso. The sensors may record the movement of the immobilized limb as well as the movement of the impaired limb.

The garment as employed in the present invention is designed to be worn by the patient over the paretic or otherwise impaired limb. For example, when an arm is affected, the garment may be a long-sleeved shirt. When a leg is affected, the garment may resemble pants.

Photonic textiles can be defined as textiles or fabrics that comprise lighting systems. The lighting systems may, for example, be light emitting diodes (LED) or organic light emitting diodes (OLED). The spatially addressable photonic textiles comprise individually addressable pixels so that a defined area of the textile may be illuminated. This may be achieved by flexible arrays of LEDs or OLEDs.

The spatially resolving pressure-sensitive textiles can be understood as textiles comprising an array of individual pressure sensors. The sensors give information about the magnitude of pressure exerted upon the surface of the garment, for example when a person is placing a grip onto a limb covered by such a garment. As the pressure-sensitive garment comprises an array of individual sensors, information about the place and the strength of the grip may be obtained.

It is possible that the garment comprises separate layers of spatially addressable photonic textiles and of spatially resolving pressure-sensitive textiles. However, it is also possible that these functionally different textiles are combined into one textile.

The processing unit may comprise signal filters for processing a multitude of simultaneous sensor signals. It may incorporate a microprocessor as a central processing unit. It transmits illumination commands to the photonic textile, meaning that it orders individual pixels to be switched on or off. It can also determine the intensity of the illumination, for example by controlling the voltage supplied to the photonic textile's pixels.

The database is a computer memory system like a RAM, ROM, flash memory, hard disks and the like. It has comparison data already stored and further records data is supplied by the various sensors of the system according to the present invention via the processing unit.

The task of resolving the data from the motion sensor or sensors into individual spatial descriptors and into the time coordinate is undertaken by the processing unit. The individual spatial descriptors represent the position of the sensor. The processed data is then stored in the database. Analogously, the data from the pressure-sensitive textiles is resolved into the spatial coordinates of x and y and pressure. The x and y coordinates represent an area of the textile where a certain pressure is applied.

The database further comprises comparison motion data resolved into the individual spatial descriptors and time. Said data represents the motion of a sensor or sensors within a specified time period. Therefore, the direction and speed of the motion of a limb with the appropriate sensors attached is modeled.

The processing unit further undertakes the task of comparing the motion data from the motion sensor or sensors to the comparison motion data in the database. When the motion data deviates from the comparison motion data by more than a predefined value, the processing unit issues illumination commands to the spatially addressable photonic textiles. As the motion data describes the motion of a limb over time, the deviation from the comparison motion data may occur either when the limb is moved too fast or too slowly or when the limb is moved in a direction or to an extent which is deemed not to be beneficial. The illumination commands may cause the photonic textiles to signal that the limb should be moved at a different speed or into a different direction. This may be done by displaying arrows, pictograms or the like. Also, based upon the pressure data, the processing unit may determine that the grip onto the limb to be mobilized is too strong and issue illumination commands to warn the user. One reason for the grip being too strong is that the limb movement is being forced against a contracture of a muscle or a joint. Undue stressing of this contracture should be avoided during mobilization of a limb.

It is possible that a plurality of individual sets of comparison motion data is stored in the database. These individual sets would represent individual exercises for the mobilization of a limb. They can be chosen at will.

With a limb movement monitoring system according to the present invention, it therefore becomes possible to mobilize or exercise a paretic or otherwise affected limb of another person, while at the same time receiving feedback about the limb movement directly on the limb. It is especially suited for inexperienced persons undertaking the mobilization.

In an advantageous embodiment of the present invention, the system further comprises a muscular activity sensor, the processing unit also receives data from the muscular activity sensor, the database also stores data from the muscular activity sensor and the processing unit also issues illumination commands to the spatially addressable photonic textiles based upon the deviation of the muscular activity data from a preset threshold.

The muscular activity sensor serves the purpose of determining the status of a muscle, especially whether a muscle is fatigued or not. It may be an electromyographical (EMG) sensor. Based upon the data from the muscle activity sensor, the processing unit may determine that the muscle or muscles on the limb to be mobilized are fatigued and that the exercise should be abandoned. This is relevant when the mobilization of the limb is not entirely passive, meaning that the person with the affected limb also tries to move the limb by himself. A continuation of the exercise with a fatigued muscle would be counterproductive. Furthermore, the muscle activity sensor can indicate whether the patient is still supporting the movement with his own muscular strength. This can be important if the mobilization is intended to be an entirely passive one.

It is also within the scope of the present invention that the system further comprises a user interface for accessing data from the database. The user interface may be in the form of a screen terminal and a keyboard. With this user interface, a user such as a medical professional may access the logged movements of the affected limb and design the exercise programs accordingly. Thus, the overall therapy will become more efficient.

In a further embodiment of the present invention, the system further comprises an external feedback system communicating motion and/or pressure data. This feedback system may be in the form of a display screen. Using data from the sensors attached to the body of the person with the impaired limb, the movement of the person's limb can be displayed in real-time. Furthermore, an exercise program may be shown on the feedback unit. Furthermore, the pressure exerted on the limb as indicated by the pressure-sensitive textile may be communicated. If a muscular activity sensor is present, then the feedback system may also communicate the status of the muscle as measured by the muscular activity sensors. These communications may take the form of optical warnings on the screen or of acoustical warnings so as not to distract from the images displayed on the screen. This enables the person to see the speed and direction of movement the limb should undertake and at the same time enables him to control the limb to make sure that it is actually being mobilized correctly.

In a further embodiment of the present invention, the spatially addressable photonic textiles of the system comprise red, green and blue illumination units. For example, the illumination units may be red, blue and greed LEDs or OLEDs. The use of color in the photonic textiles is beneficial in that a greater range of information may be conveyed. For example, the photonic textiles may display an area where a person should place his grip on the limb to be mobilized in one color and the direction of movement of the limb in arrows of a different color. Furthermore, the textiles may indicate that the grip of a person on the limb is too strong by changing the color of the respective area to a warning color, such as red.

In a further embodiment of the present invention, the spatially resolving pressure-sensitive textiles of the system comprise piezoresistive fabrics. The use of such fabrics allows for a very flexible and lightweight pressure-sensitive fabric. Piezoresistive fabrics can be realized by using a polymer fabric such as a polyurethane fabric coated with carbon-loaded rubber and commercially available electroconductive yarn. Alternatively, these fabrics can be coated with conducting polymers such as polypyrrole. These fabrics behave as strain gauge sensors and show piezoresistive properties in response to an external mechanical stimulus. These fabrics also have the advantage of being machine washable, thus improving the hygiene of the product.

In a further embodiment of the present invention, the signals from the at least one motion sensor, from the pressure-sensitive textiles and/or the commands to the spatially addressable photonic textiles are transmitted wirelessly. The wireless transmission may, for example, be undertaken via a variety of commercially available wireless transmission technologies like Bluetooth, infrared, WLAN (wireless local area network) and the like. It is also possible to use a proprietary protocol. By eliminating the need for cables, the convenience of use for the patient is increased as well as the safety, because the patient cannot stumble over these cables any more.

In a further embodiment of the present invention, the system further comprises a glove comprising spatially resolving pressure-sensitive textiles, said glove transmitting pressure data to the processing unit. The glove is intended to be worn on the hand of the person mobilizing the affected limb. By the use of such a glove the information about the grip strength can be obtained more accurately, thus leading to a more comfortable mobilization for the person with the affected limb. The pressure-sensitive textiles may be placed on the tips of the fingers. Additionally, or alternatively, they may be placed over knuckle joints to determine the flexing of a joint.

In a further embodiment of the present invention, the system further comprises sensors selected from the group comprising skin perspiration sensors, pulse sensors, blood pressure sensors and/or blood oxygen level sensors, and the sensors further provide input to the processing unit. These sensors may provide further information regarding the status of the patient. They may especially relate to the stress status of the person. For example, skin perspiration sensors relate to the electrical conductivity of the skin surface, which changes according to the level of perspiration caused by stress and fatigue. Pulse sensors, blood pressure sensors and/or blood oxygen level sensors may be integrated into one sensor system which can be worn, for instance, on the tip of a finger or can be attached to an ear lobe with a clip. They are useful in providing data related to the circulatory system of the patient. By monitoring the stress status of the person, the exercise unit can be terminated in time before overexerting the person.

A further embodiment of the present invention concerns a process for monitoring limb movement by a system according to the present invention, comprising the steps of:
a) calibrating the at least one motion sensor by bringing the at least one motion sensor into a predetermined position and registering the output signal from the at least one motion sensor in this position
b) gathering motion sensor and pressure sensor output signals
c) assigning the motion sensor output signals to a position and a movement of the respective at least one motion sensor
d) storing the position, movement and pressure signals in a database e) comparing the position, movement and pressure signals which have been stored within a predetermined timeframe to predetermined position and movement data in the database
f) deciding whether predefined boundary conditions with respect to position, movement and/or pressure are exceeded and communicating this.

When a limb movement monitoring system according to the present invention is used, the person with the limb to be moved firstly puts on the garment comprising the photonic textiles and the pressure-sensitive textiles over the respective limb. If the motion sensor or motion sensors are not also incorporated in the garment, they are then attached to the person with the limb to be moved. The motion sensor or sensors can be attached to the limb directly and additionally to other parts of the person's body. The sensors attached to the limb may be placed above and below a joint of the limb. The same applies for the one or more muscular activity sensors which may also be present. They are placed on the muscles of the limb to be mobilized. The calibration of the signals as described in step a) serves to generate a good set of starting positions for the detection of limb movement.

The processing unit issues illumination commands to the photonic textiles to the effect that the textile lights up where a second person such as either a medical professional or a layman like the first person's partner should place his hands onto the limb of the first person. The position of the hands of the second person and their grip strength are transmitted to the processing unit via the spatially resolving pressure-sensitive textile.

In step b) of the process, the motion sensor and pressure sensor output signals are gathered. This is undertaken by the processing unit. In conjunction with this, in step c) the signals are resolved into spatial coordinates and into time and pressure, respectively. Step d) describes the storing of the resolved signals into the database. Step e) describes the comparison of the data set to a predetermined data set in the database. This predetermined data set represents a movement of a respective limb at a certain speed. Therefore, it can be viewed as an exercise program. In this step the deviation of the collected signals from the predetermined signals is calculated. In other words, it is calculated whether the movement of the limb, within a certain tolerance, is according to the exercise program.

Should it be determined that predefined boundary conditions of limb position, movement and/or grip pressure are exceeded (step f)), then this is communicated. The communication may be undertaken via messages displayed on the photonic textiles. For example, arrows may be displayed indicating the correct direction for the limb movement or the photonic textile may adopt a warning color, such as red.

In a further embodiment of the present invention, the process further comprises a feedback system which additionally communicates excercises for the limbs to be moved. The feedback system may be in the form of a display. The display would then show an image or image sequence with the desired motion of the limb and at the same time the present position of the limb. By means of this the desired exercise becomes more clearly understood.

FIG. 1 is a block diagram of the components of a system according to the present invention, which shows the interactions between them. The processing unit (CPU, reference numeral 5) is provided with sensory input from a motion sensor (1), from a pressure sensor in the pressure-sensitive textiles (3) and from a muscular activity sensor (4). After processing the data and resolving it into spatial, time and pressure coordinates, the data is written into the database (6).

The processing unit (5) compares the data to comparison data. The comparison data can represent an exercise for the limb to be mobilized. If the deviation of the actual data from the comparison data exceeds a predetermined threshold, a warning is given via illumination of the spatially addressable photonic textiles (2) or additionally via a message on the display unit (8). Furthermore, the display unit (8) can give feedback about the position of the limb to be mobilized by displaying the actual position and the position where it should be. The photonic textiles (2) may also further be addressed by the processing unit (5) to indicate positions where a person mobilizing the limb to be mobilized should place his hands. Via a user interface (7), a medical professional may access the data from the database (6) to check the progress of the mobilization of the limb. Furthermore, new exercise programs may be entered into the database (6), using the user interface (7).

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this application and in the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. Limb movement monitoring system, comprising:
   a motion sensor (1),
   a garment comprising spatially addressable photonic textiles (2) and spatially resolving pressure-sensitive textiles (3),
   a processing unit (5) which receives data from the motion sensor (1) and from the spatially resolving pressure-sensitive textiles (3) and which issues illumination commands to the spatially addressable photonic textiles (2),
   a database (6) in communication with the processing unit (5), wherein
   the database (6) stores data from the motion sensor (1) resolved into individual spatial descriptors and time,
   the database (6) stores data from the pressure-sensitive textiles (3) resolved into at least the categories of x and y coordinates and pressure,
   the database (6) furthermore comprises comparison motion data resolved into individual spatial descriptors and time,
   the processing unit (5) compares the motion data from the motion sensor to the comparison motion data in the database (6), and
   the processing unit (5) issues illumination commands to the spatially addressable photonic textiles (2) based upon the deviation of the motion data from the comparison motion data and the deviation of the pressure data from a preset threshold.

2. System according to claim 1, further comprising a muscular activity sensor (4), wherein the processing unit (5) also receives data from the muscular activity sensor (4), the database (6) also stores data from the muscular activity sensor (4) and the processing unit (5) also issues illumination commands to the spatially addressable photonic textiles (2), based upon the deviation of the muscular activity data from a preset threshold.

3. System according to claim 1, further comprising a user interface (7) for accessing data from the database.

4. System according to claim 1, further comprising an external feedback system (8) communicating motion and/or pressure data.

5. System according to claim 1, wherein the spatially resolving pressure-sensitive textiles (3) comprise piezoresistive fabrics.

6. System according to claim 1, wherein the signals from the at least one motion sensor (1), from the pressure-sensitive textiles (3) and/or the commands to the spatially addressable photonic textiles (2) are transmitted wirelessly.

7. System according to claim 1, further comprising a glove comprising spatially resolving pressure-sensitive textiles, wherein the glove transmits pressure data to the processing unit (5).

8. System according to claim 1, further comprising sensors selected from the group comprising skin perspiration sensors, pulse sensors, blood pressure sensors and/or blood oxygen level sensors, wherein the sensors further provide input to the processing unit (5).

9. Process for monitoring limb movement by a system according to claim 1, comprising the steps of:
   a) calibrating the at least one motion sensor (1) by bringing the at least one motion sensor (1) into a predetermined position and registering the output signal from the at least one motion sensor (1) in this position
   b) gathering motion sensor and pressure sensor output signals
   c) assigning the motion sensor output signals to a position and a movement of the respective at least one motion sensor
   d) storing the position, movement and pressure signals in a database (6)
   e) comparing the position, movement and pressure signals which have been stored within a predetermined timeframe to predetermined position and movement data in the database (6)
   f) deciding whether predefined boundary conditions with respect to position, movement and/or pressure are exceeded and communicating this.

10. Process according to claim 9, further comprising a feedback system (8) which additionally communicates exercises for the limbs to be moved.

* * * * *